US008679435B2

(12) United States Patent
Kita et al.

(10) Patent No.: US 8,679,435 B2
(45) Date of Patent: Mar. 25, 2014

(54) GENERATION OF SULFUR TRIOXIDE AND SULFURIC ACID

(75) Inventors: Dieter Kita, Blackstone, MA (US);
Yongquan Li, Schenectady, NY (US);
Jeffrey Socha, Boylston, MA (US);
Bryan A. Marcotte, Blackstone, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 0 days.

(21) Appl. No.: 13/251,754

(22) Filed: Oct. 3, 2011

(65) Prior Publication Data

US 2012/0087856 A1    Apr. 12, 2012

Related U.S. Application Data

(63) Continuation of application No. 12/463,795, filed on May 11, 2009, now Pat. No. 8,052,949.

(51) Int. Cl.
*B01D 53/14* (2006.01)
*B01D 53/56* (2006.01)
*C01B 17/00* (2006.01)
*C01B 17/74* (2006.01)

(52) U.S. Cl.
USPC ........ 423/222; 423/210; 423/241.1; 423/511; 423/532

(58) Field of Classification Search
None
See application file for complete search history.

(56) References Cited

U.S. PATENT DOCUMENTS

| | | | |
|---|---|---|---|
| 2,949,345 A | 8/1960 | Clauss | |
| 3,367,747 A | 2/1968 | Sieth et al. | |
| 3,404,956 A | 10/1968 | Drechsel et al. | |
| 3,615,196 A | 10/1971 | Welty et al. | |
| 3,904,387 A | 9/1975 | Kertamus et al. | |
| 4,622,105 A * | 11/1986 | Liu et al. | 205/784 |
| 5,196,038 A | 3/1993 | Wright | |
| 5,264,200 A | 11/1993 | Felthouse et al. | |
| 5,338,515 A * | 8/1994 | Dalla Betta et al. | 422/95 |
| 5,582,802 A | 12/1996 | Spokoyny et al. | |
| 5,678,493 A | 10/1997 | Kelley et al. | |

(Continued)

FOREIGN PATENT DOCUMENTS

| | | | |
|---|---|---|---|
| JP | 2001289783 | * | 10/2001 |
| SU | 719687 | | 1/1978 |

OTHER PUBLICATIONS

Endres, Hannis-Erik et al, "A Test System for Gas Sensors". Sensors and Actuators B 23, 163-172 (1995).

(Continued)

*Primary Examiner* — Melvin C Mayes
*Assistant Examiner* — Sheng H Davis
(74) *Attorney, Agent, or Firm* — Chapin IP Law, LLC

(57) ABSTRACT

Configurations herein include a novel process and apparatus for generating and maintaining sulfur trioxide gas. The generation system and process operate to provide sulfur trioxide calibration gas for calibrating sulfur trioxide detection devices. The system and process provides a known, concentration of sulfur trioxide gas via a heated catalyst, which enables accurate calibration of measurement equipment. The system functions in part by controlling temperature, amount of moisture, residence time, catalyst selection, diluting generated sulfur trioxide and by locating the sulfur trioxide generator at a point of injection of a sulfur trioxide detection system.

23 Claims, 6 Drawing Sheets

(56) References Cited

U.S. PATENT DOCUMENTS

| | | |
|---|---|---|
| 6,396,056 B1 | 5/2002 | Lord et al. |
| 6,399,040 B1 | 6/2002 | Dafft et al. |
| 6,572,835 B1 * | 6/2003 | MacArthur et al. .......... 423/532 |
| 2007/0007147 A1 * | 1/2007 | Lahoda .................... 205/637 |
| 2007/0260072 A1 | 11/2007 | Harrod et al. |
| 2008/0213913 A1 | 9/2008 | Alberti et al. |
| 2008/0226540 A1 | 9/2008 | Felthouse et al. |

OTHER PUBLICATIONS

Rawlings, W.T., et al., "A Quantum Cascade Laser Sensor for SO2 and SO3 for Application to Combustor Exhaust Streams" Applied Optics 44 (31), 6635-5543 (Nov. 2005).

International Search Report mailed Jun. 18, 2010 in corresponding International Patent Application No. PCT/US10/31786.

* cited by examiner

GENERATION OF SULFUR TRIOXIDE AND SULFURIC ACID

CROSS-REFERENCE TO RELATED APPLICATIONS

This application is a continuation of U.S. patent application Ser. No. 12/463,795, filed May 11, 2009, now U.S. Pat. No. 8,052,949 which is related to U.S. patent application Ser. No. 12/463,915, filed May 11, 2009, entitled "ENVIRONMENTAL CONTROL OF FLUID SAMPLES, CALIBRATION, AND DETECTION OF CONCENTRATION LEVELS," the entire teachings of which are incorporated herein by this reference.

BACKGROUND

Emissions from fossil fuel combustion facilities, such as flue gases of coal-fired utilities and municipal solid waste incinerators, typically include sulfur trioxide ($SO_3$). Coal and petroleum fuels usually contain sulfur compounds. Combusting such sulfur containing compounds generates sulfur dioxide ($SO_2$). Combustion facilities typically operate pollution control devices, which are catalysts, to remove nitrogen monoxide (NO). A side effect of NO control devices (Selective Catalytic Reduction SCR) is the generation of sulfur trioxide. During the removal of NO, a portion of the sulfur dioxide emission is typically oxidized resulting in sulfur trioxide, which escapes the pollution control devices. Sulfur trioxide has a strong affinity for water, and, in the presence of moisture, rapidly becomes sulfuric acid ($H_2SO_4$).

Sulfur trioxide emissions are undesirable for several reasons. Sulfur trioxide and/or sulfuric acid exiting a stack or chimney can result in pollution. Sulfuric acid is a common agent in acid rain. Sulfur trioxide can be very corrosive to equipment used in combustion facilities. Sulfur trioxide exiting a stack can appear as a blue plume, that is, exhaust smoke adding opacity and visual air pollution. Selective catalytic reduction processes used to reduce other pollutants can have the effect of creating higher sulfur trioxide levels in flue gases. Such higher levels of sulfur trioxide have adversely affected removal of certain pollutants. For example, mercury is commonly removed from flue gases using activated carbon as part of an adsorption process. With higher levels of sulfur trioxide present during the adsorption process, the percent of mercury removed from flue gases decreases. Because of the potential environmental pollution, corrosion to combustion equipment, and the adverse effect on other pollution control systems, it is important to measure, monitor, and control sulfur trioxide emissions.

SUMMARY

There are several types of detection systems that can be used to measure sulfur trioxide. Such systems include Fourier transform infrared (FTIR) spectroscopy, tunable diode laser spectroscopy, acid dew-point, conversion and fluorescence, filter correlation, and cavity ring-down. Some of these systems measure sulfur trioxide directly, while others measure sulfur trioxide indirectly. The acid dew point approach infers $H_2SO_4$. For example, it only detects an acid dewpoint, which in conjunction with a water concentration and gas temperature information, can be used to calculate $H_2SO_4$. Additionally, a conversion and fluorescence system requires conversion of sulfur trioxide to sulfur dioxide, and then the measurement of sulfur dioxide is made before and after the sulfur trioxide converter in order to infer the sulfur trioxide amount. Some of these systems have a poor detection limit, meaning that such systems cannot measure sulfur trioxide amounts below a certain concentration or relative proportion of flue gases.

One relevant inaccuracy to appreciate is that the chemical industry, by and large, labels both $H_2SO_4$ and $SO_3$ with the term sulfur trioxide. In most conventional applications, distinguishing between the two compounds is not important, and so this inaccurate identification exists. This means that there are cases of systems that claim to measure sulfur trioxide, when in reality this is not a direct measurement. Such systems directly measure a concentration of sulfuric acid and then infer or calculate what sulfur trioxide amounts existed before conversion or condensation to sulfuric acid. As used herein to discuss certain embodiments, directly measuring $SO_3$ means measuring a sample of sulfur trioxide gas as opposed to measuring sulfuric acid.

Typically, equipment used to detect sulfur trioxide must be calibrated. Calibration can be important for several reasons. The harsh conditions of a combustion system can effect sensitive measurement equipment. Without proper and routine calibration, errors in detection equipment can amplify and cause erroneous results. For proper calibration of equipment, a detection system may need a source for generating sulfur trioxide calibration gas.

Generating sulfur trioxide calibration gas is challenging. Sulfur trioxide gas is unstable and difficult to maintain. As such, sulfur trioxide gas is generally not available for purchase. For example, sulfur trioxide is not sold as a gas that is isolated and stored in a tank or cylinder. The lack of available sources of sulfur trioxide exists because sulfur trioxide quickly converts to sulfuric acid in the presence of water, and/or at low temperatures. In contrast, sulfur dioxide gas is stable at room temperature, and is generally available for purchase. Thus, for systems that directly measure sulfur trioxide, and use it for calibration, providing sulfur trioxide gas for calibrating equipment is an obstacle.

Techniques discussed herein significantly overcome the challenges in providing sulfur trioxide calibration gas. For example, embodiments herein include a novel process and apparatus for generating and maintaining sulfur trioxide gas. The generator process includes receiving a known concentration, or quantity, of sulfur dioxide gas. For example, a source stores a known concentration of sulfur dioxide gas. By drawing sulfur dioxide gas at a known rate from the source, the generator process receives a known concentration of sulfur dioxide gas. In addition to receiving the sulfur dioxide, the generator process includes receiving an oxidizing agent gas, for example, oxygen or air. In one embodiment, the oxidizing agent such air, oxygen, etc., and the sulfur dioxide can be received from the same gas cylinder containing both the sulfur dioxide and air. In accordance with other embodiments, the sulfur dioxide and air can be received from different sources.

Subsequent to receipt of the sulfur dioxide and agent, the generator process passes the known concentration of received sulfur dioxide gas and the received oxidizing agent gas through a catalyst. For example, the generator process directs the gases to a surface area of a metallic catalyst. The generator process heats the catalyst, for example, to a sufficient temperature, to react the known concentration of sulfur dioxide gas and the oxidizing agent gas to produce a known concentration of sulfur trioxide gas. The generator process then maintains the sulfur trioxide gas in a gaseous state. The benefit of maintaining sulfur trioxide in a gaseous state is that the sulfur trioxide gas can be delivered for use as a calibration gas for a system requiring sulfur trioxide.

Additional embodiments of the generator process include maintaining the sulfur trioxide gas in a gaseous state by diluting generated sulfur trioxide gas with heated air, and maintaining the air at an elevated temperate that is approximately the temperature of the catalyst or above a condensation/conversion point of sulfuric acid. Diluting the sulfur trioxide gas with heated air, that is substantially free of water, slows down the further reactions of sulfur trioxide reduces a possibility that the sulfur trioxide converts into sulfuric acid. Perhaps more importantly, dilution of the sulfur trioxide allows adjustment of the concentration of sulfur trioxide in an outputted calibration gas sample. In one embodiment, diluting the produced sulfur trioxide gas enables creation of calibration gases having different concentrations of sulfur trioxide. The different concentrations of sulfur trioxide gas can be used to perform multi-point calibration of a respective analyzer system.

In another embodiment, the generator process delivers the generated and maintained known concentration of sulfur trioxide gas to a sulfur trioxide detection device. As mentioned above, the known concentration of the sulfur trioxide gas enables calibration of the detection device. The detection device can be a Fourier transform infrared (FTIR) spectroscopy device, a tunable diode laser used with an optical cell, or other suitable device for identifying chemicals and/or concentrations of chemicals.

In another embodiment, the generator process adjusts the temperature of the catalyst based on a flow rate of the sulfur trioxide gas through the catalyst. Keeping the catalyst at a constant temperature while varying the flow rate will affect conversion efficiency of sulfur dioxide to sulfur trioxide. If a flow rate increases, while temperature remains constant, then conversion efficiency drops. To maintain conversion efficiency, the catalyst can be heated to a higher temperature for higher flow rates of the known concentration of sulfur dioxide through the catalyst.

As mentioned above, one of the primary uses of generated sulfur trioxide gas is for use as a calibration gas. Calibration is more accurate with higher concentrations of sulfur trioxide, and by having a known concentration of the calibration gas. In one embodiment, the generator process adjusts temperature based on flow rate to maintain a conversion efficiency that is above about 99%.

In addition to the method as discussed above, embodiments herein also include an apparatus or system for generating and maintaining sulfur trioxide gas, in other words, a sulfur trioxide generator. The generator includes an input to receive a known concentration of sulfur trioxide gas and an oxidizing agent gas. For example, the generator uses one or more gas tanks for storing and delivering the gases. The generator includes a chamber that encloses a catalyst, and a heater or heat source to heat the chamber and/or catalyst. The chamber can be constructed to expose the known concentration of sulfur dioxide gas and the oxidizing agent gas to the catalyst. The catalyst is a solid material such as metal, and thus has a surface area. The catalyst can be any material that reduces the energy required to react sulfur dioxide with an oxidizing gas to create sulfur trioxide. For example, the catalyst can be a metallic catalyst such as platinum or palladium. The generator includes a heater configured to heat the catalyst to react the known concentration of sulfur dioxide gas and the oxidizing agent gas into a known concentration of sulfur trioxide gas.

According to embodiments herein, an output port of the sulfur trioxide generator emits the known concentration of sulfur trioxide gas for calibration testing. A sulfur trioxide gas delivery conduit, connected to the output, maintains sulfur trioxide gas in a gaseous state for use as a calibration gas. As briefly mentioned above, either before of after conversion of the sulfur dioxide into sulfur trioxide, the generator or the gas delivery conduit can be configured to dilute the sulfur trioxide gas to change a relative concentration of the sulfur trioxide in a calibration gas and reduce a potential for further reaction of the sulfur trioxide.

In another embodiment, the gas delivery conduit connects to a sulfur trioxide detection device. Both the gas delivery conduit and the detection device can be heated to prevent further reaction of the sulfur trioxide into $H_2SO_4$. The gas delivery conduit and the detection device can include independently operating heat sources, or both components can be located within a common heated environment. The heated environment or heat source maintains the known concentration of sulfur trioxide gas at or above a threshold temperature such as a condensation/conversion temperature at which the sulfur trioxide will tend to convert into sulfuric acid in the presence of water. Accordingly, heating of the sulfur trioxide (above the condensation/conversion temperature) can prevent conversion of the sulfur trioxide into sulfuric acid.

The entire generator system can be housed within a combustion gas probe, wherein the probe is configured to attach to a combustion system or exhaust gas stack, or exhaust ductwork upstream of the stack.

Embodiments herein enable supplying of a known concentration of sulfur trioxide to calibrate equipment that directly measures sulfur trioxide in sample gases retrieved from a source such as a flue.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments herein include a novel process and apparatus for generating and maintaining sulfur trioxide gas. The generation system and process operate to provide sulfur trioxide calibration gas for calibrating sulfur trioxide detection devices. The system and process provides a known concentration of sulfur trioxide gas, which enables accurate calibration of measurement equipment. The system functions in part by utilizing a heated catalyst to generate a gas having a known concentration of sulfur trioxide, diluting the generated sulfur trioxide gas, controlling temperature and amount of moisture before and/or after conversion/dilution, and by locating the sulfur trioxide generator at a point of injection of a sulfur trioxide detection system that directly measures sulfur trioxide.

Figure 1:
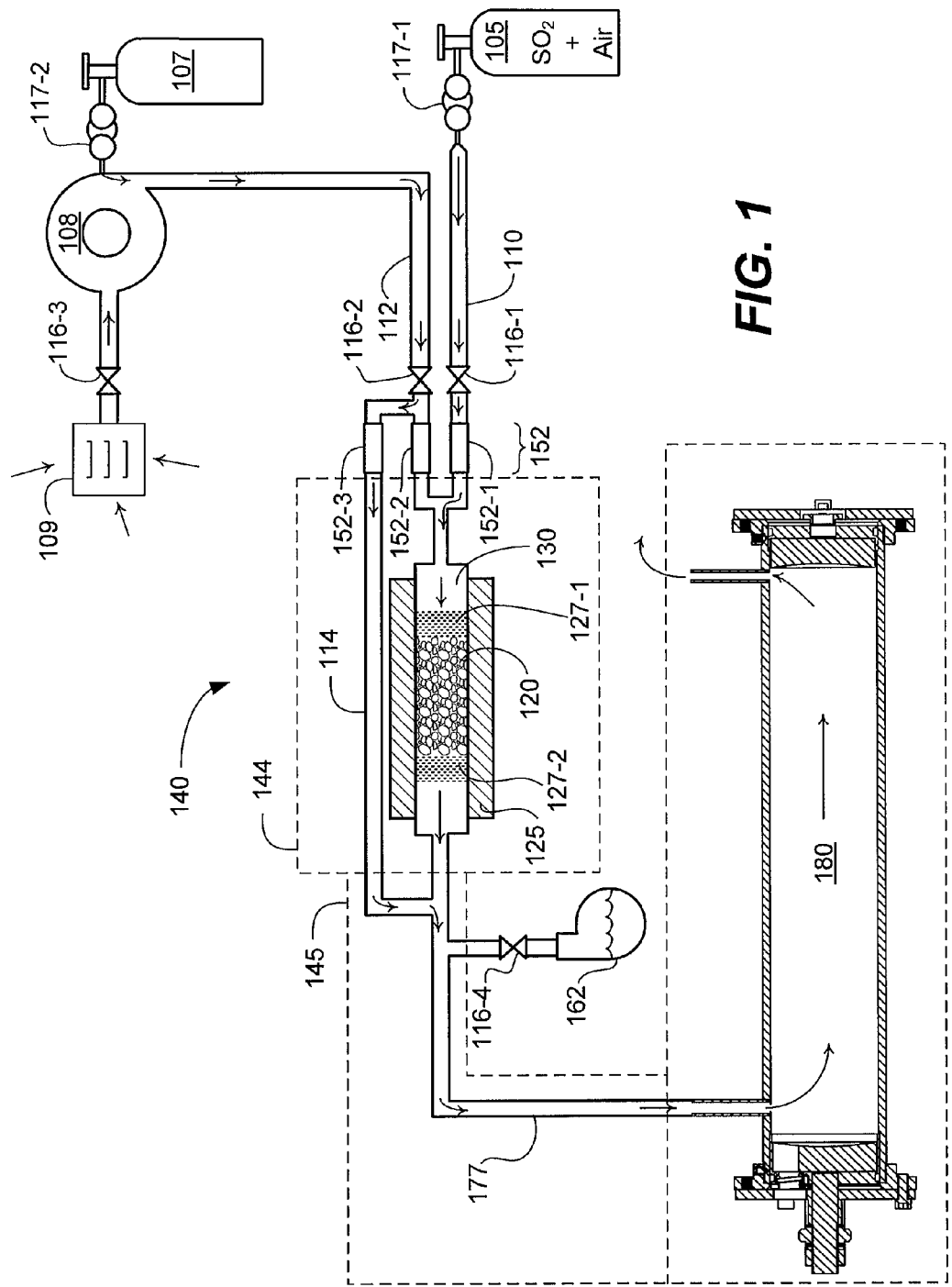
FIG. 1 is a diagram of a sulfur trioxide generation system according to embodiments herein.

Now, more specifically, FIG. 1 depicts a sulfur trioxide generator 140. Generator 140 includes source 105. In one embodiment, source 105 is a cylinder containing a gaseous mixture of sulfur dioxide and air. Valve 117-1 controls a flow of gas from source 105 into conduit 110. Additionally, valve 116-1 and mass flow controller 152-1 control a flow of the gas (received from source 105) into oxidizing chamber 130.

Oxidizing chamber 130 includes catalyst 120. As will be discussed in more detail later in this specification, catalyst 120 in oxidizing chamber 130 provides a (relatively water-free environment (e.g., including a temperature controlled metallic surface area) for reacting the received sulfur dioxide gas and air (the air includes oxygen) into a sulfur trioxide gas of known concentration.

In one embodiment, heater 125 can be used to heat the catalyst 120 and received gas (e.g., the sulfur dioxide gas received from source 105) to aid in conversion of the sulfur dioxide into sulfur trioxide in the oxidizing chamber 130. For example, the heater 125 heats the oxidizing chamber 130 to a desired temperature.

The sulfur trioxide generator 140 outputs the produced sulfur trioxide calibration gas into conduit 177. Conduit 177 thus receives sulfur trioxide gas (e.g., a calibration gas) generated by the oxidizing chamber 130. Conduit 177 delivers sulfur trioxide gas to optical cavity 180, where the generated sulfur trioxide calibration gas is then used to calibrate an optical system associated with optical cavity 180. After calibration, the optical system can be used to detect an absorption of optical energy in a sample to determine a concentration of sulfur trioxide in the gas sample. In one embodiment, the optical cavity 180 is a Herriot type multi-pass optical cell for use with laser spectroscopy. Additional details of the sulfur trioxide detection system that is calibrated with the generated sulfur trioxide gas can be found in the related application incorporated by reference.

Note that in addition to calibrating optical systems, the calibration gas generated herein can be used calibrate any type of sulfur trioxide monitoring system.

Also, as shown, the generator 140 can optionally include hydration module 162 to hydrate the sample produced by the sulfur trioxide generator 140.

As previously discussed, the source 105 can be configured to supply a gaseous mixture of sulfur dioxide and air to the sulfur trioxide generator 140. In one embodiment, the gaseous mixture includes 100 parts-per-million of sulfur dioxide (i.e., the gas from source 105 has a known concentration of sulfur dioxide) and 1 part-per-million of water. The gaseous mixture provided by source 105 is thus mostly air.

As will be discussed in more detail below, embodiments herein include providing a water-free environment or humidity controlled environment for conversion of sulfur dioxide in the gaseous mixture into sulfur trioxide. The presence of a small amount of water in the gaseous mixture of sulfur dioxide and air may result in a portion of the sulfur dioxide converting into sulfuric acid. However, the small amount of water (e.g., the 1 part-per-million received from the source 105) and the inability for water to contaminate the gaseous mixture passing through conduit 110, oxidizing chamber 130, conduit 177, etc., ensures that the sulfur trioxide gas used for calibration is of a known concentration. Thus, embodiments herein include preventing exposure of the sulfur dioxide gas, sulfur trioxide gas, agent gas, etc., to water.

The sample calibration gas of sulfur trioxide outputted by oxidizing chamber 130 can be diluted via dilution gas received from source 107. For example, the mass flow controller 152-3 can be configured to control a rate of diluting the sulfur trioxide gas of known concentration as outputted by the oxidizing chamber 130.

In one embodiment, the mass flow controller 152-3 dilutes the sulfur trioxide gas sample by a first amount to calibrate optical cavity 180 and related optical system at a first concentration setting; the mass flow controller 152-3 dilutes the sulfur trioxide gas sample by a second amount to calibrate optical cavity 180 and related optical system at a second concentration setting; the mass flow controller 152-3 dilutes the sulfur trioxide gas sample by a first amount to calibrate optical cavity 180 and related optical system at a third concentration setting.

Generator 140 can maintain environment 144 to a temperature of between 225 and 600 degrees Celsius to facilitate conversion. The generator 140 can maintain environment 145 such as conduit 177 at a cooler temperature such as between 200 and 300 degrees Celsius.

It may be advantageous to maintain source 105 and/or source 107, mass flow controllers, and hydrator 108 at room temperature, separate from or outside of the heated environments 144 and 145.

In one embodiment, generator 140 maintains heated environments 144 and 145 at a temperature above a condensation/conversion point (e.g., threshold temperature value) of sulfuric acid. Environment 145 can include conduit 177 and/or optical cavity 180. Thus, any or all portions of the system as described herein can be heated to facilitate conversion of sulfur dioxide and/or use of sulfur trioxide gas as a calibration gas.

Figure 2:
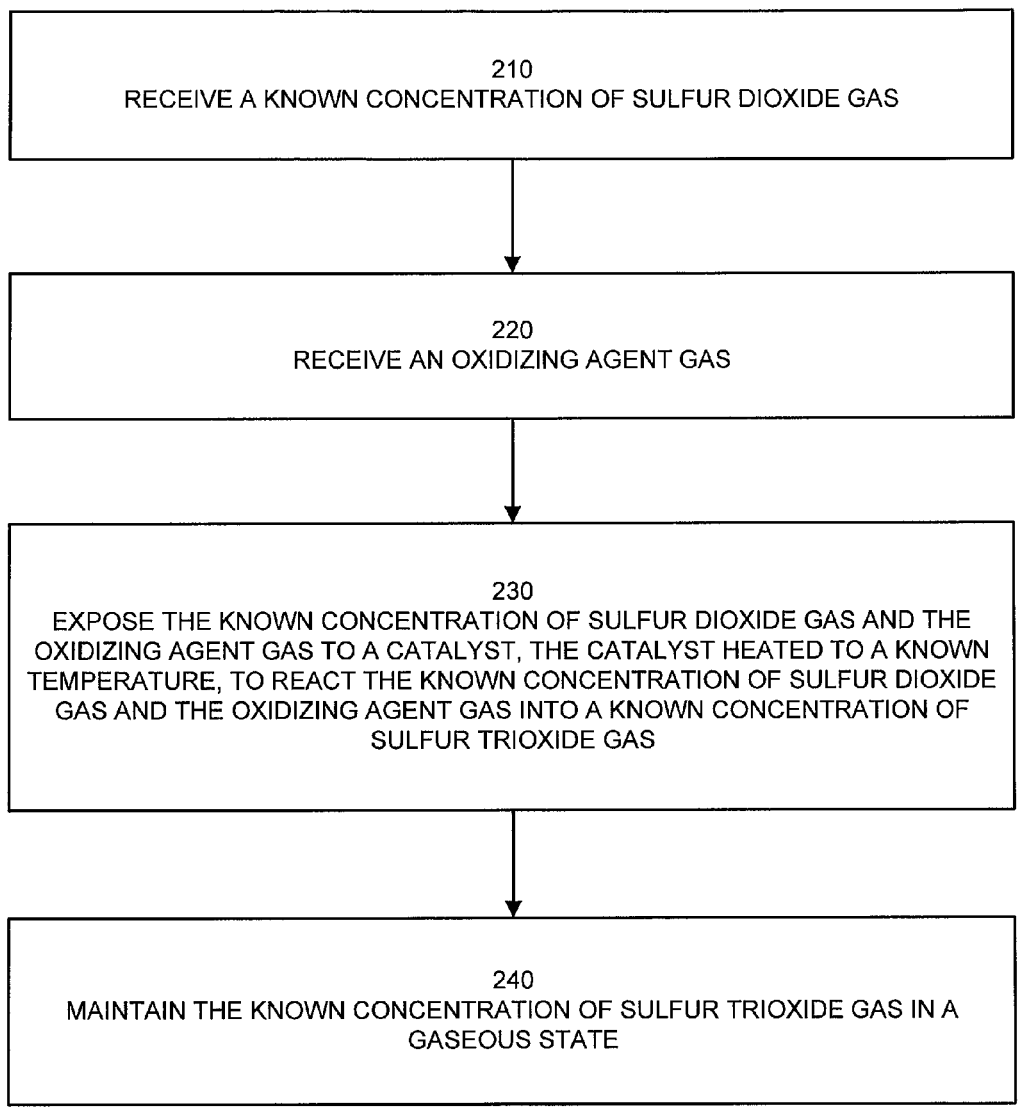
FIG. 2 is a flow chart of a sulfur trioxide generation process according to embodiments herein.
Figure 3:
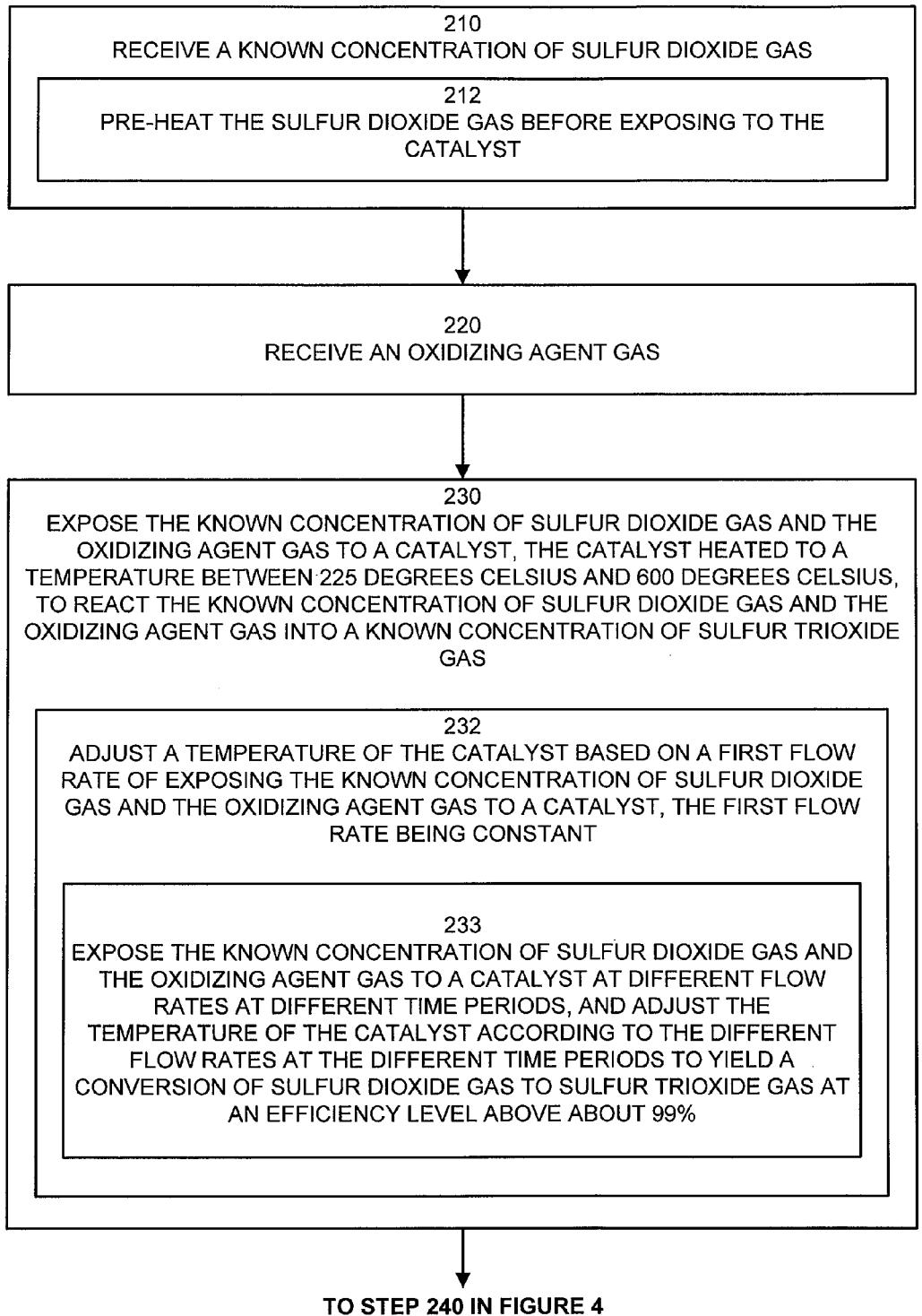
FIGS. 3-4 are flow charts of a sulfur trioxide generation process according to embodiments herein.
Figure 4:
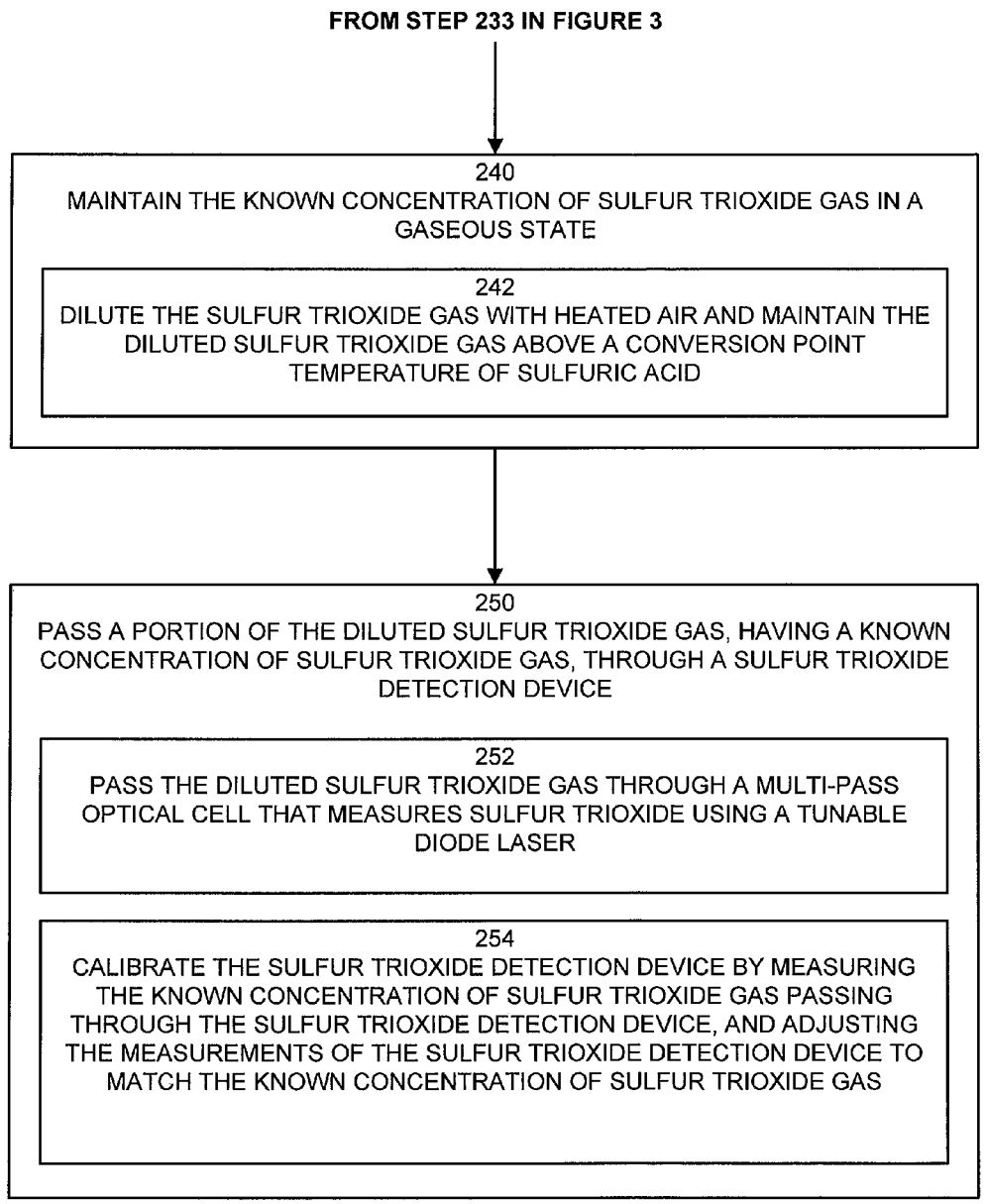

FIGS. 2-4 depict flowcharts that illustrate generator processes that generator 140 executes according to embodiments herein. Referring to FIG. 2, in step 210, generator 140 receives a known concentration of sulfur dioxide gas, such as from sulfur dioxide from source 105. Sulfur dioxide gas is generally stable at ambient temperatures, and thus can be stored in a tank or canister adjacent to chamber 130. A storage container of sulfur dioxide gas may be pure sulfur dioxide gas, or may contain some oxygen, air, or inert gases as previously mentioned. Regardless of the storage method, according to one embodiment, a concentration of the stored sulfur dioxide gas is known. For example, a known concentration is indicated as a numeric value in parts per million (ppm), or parts per billion (ppb).

In step 220, generator 140 receives an oxidizing agent gas. In this example embodiment, the oxidizing agent such as oxygen can be received through conduit 110 from source 105. As mentioned above, oxygen can be stored in tank 105 along with sulfur dioxide. Thus, the sulfur dioxide and agent can be received from the same source. In this embodiment, oxygen is premixed with sulfur dioxide in tank 105 or other suitable sulfur dioxide source. Mass flow controller 152-2 is closed to prevent flow of additional oxidizing agent gases. Both the sulfur dioxide gas and oxidizing agent flow through conduit 110. Mass flow controller 152-1 controls and/or measures the flow rate of the sulfur dioxide/oxidizing agent mix prior to being exposed to the catalyst 120 in oxidizing chamber 130.

As mentioned above, the sulfur dioxide and oxygen are alternatively received from different sources. In other words, it is optional to have an oxygen supply separate from the sulfur dioxide supply. However, maintaining the gases in the same cylinder (such as in source 105 as opposed to different sources) may be advantageous as this former arrangement can simplify the system.

In this latter embodiment, when the sulfur dioxide and agent are received from different sources, valve 116-2 enables passage of gas to chamber 130 and/or conduit 114. Air dryer 108 can optionally dry gases from any oxygen source. In one embodiment, generator 140 includes source 107. Source 107 stores an oxidizing agent such as oxygen separate from a container of sulfur dioxide 105. In such an embodiment, mass flow controllers 152-1 and 152-2 control and measure a flow rate of sulfur dioxide gas and the oxidizing agent gas respectively. Mass flow controllers 152-1 and 152-2 also control mixing of the gases prior to being exposed to catalyst 120.

In yet another alternative embodiment, instead of receiving oxidizing agent from source 107, generator 140 can draw or pull air from an environment surrounding generator 140 through vent 109, and runs the air through air dryer 108 to remove moisture from the oxidizing agent gas before mixing with sulfur dioxide gas. Valves 116-3 and 117-2 control a source of the oxidizing agent gas.

The received sulfur trioxide and oxidizing agent gas received by oxidizing chamber 130 are substantially free of water. For example, the cylinder 105 contains sulfur dioxide, air, and less than about 1 ppm of water.

In step 230, generator 140 exposes the received known concentration of sulfur dioxide gas and the received oxidizing agent gas to catalyst 120 in any manner as discussed above. The catalyst 120 can be metallic material, or mixture of materials, such as palladium, platinum, stainless steel, iron oxide, vanadium, or other suitable metallic or non-metallic substance that lowers the energy necessary to oxidize sulfur dioxide into sulfur trioxide. Thermodynamically, sulfur dioxide in the presence of oxygen tends to become sulfur trioxide because the energy state of sulfur trioxide is lower than that of sulfur dioxide. There is no spontaneous conversion, however, because there is an energy barrier to overcome before any conversion. Using a catalyst, the energy barrier is reduced by lowering the activation energy, which enables this exothermic reaction to proceed at lower temperatures.

Catalyst 120 can be configured in a number of ways to facilitate generation of sulfur trioxide gas. For example, as mentioned above, catalyst 120 resides in a path of travel such that the sulfur dioxide and oxidizing agent gas mix with each other and are exposed to a surface of material in the catalyst 120. In one embodiment, catalyst 120 comprises a packing of loose metallic material (e.g., particles, powder, chips, granules, etc.) to create a filter or pathway through which the sulfur dioxide and oxidizing agent gas must pass. Frits 127-1 and 127-2 hold the metallic particles in place. Packing of particles using frits 127 provides a substantial surface area facilitating a reaction of the sulfur dioxide into sulfur trioxide.

Generator 140 uses heater 125 to heat catalyst 120 to a temperature between 225° C. and 600° C., to facilitate the reaction of the known concentration of sulfur dioxide gas and the oxidizing agent gas into a known concentration of sulfur trioxide gas. Heater 125 can be any heat source such as a cartridge heater. In the absence of a surface catalyst, sulfur dioxide mixed with oxygen can convert to sulfur trioxide when sufficiently heated, such as above about 600° C. In the presence of catalyst 120, however, the temperature needed for oxidizing sulfur dioxide can be substantially lower. For example, a temperature between 225° C. and 600° C. is sufficient to generate sulfur trioxide in the presence of the catalyst 120.

According to one embodiment, the concentration of generated sulfur trioxide gas is known, in part, because the concentration of sulfur dioxide gas is known, and a reaction conversion efficiency is known by controlling parameters of generator 140.

The reaction of sulfur dioxide into sulfur trioxide is a one-to-one reaction. If an initial concentration of sulfur dioxide gas is on the order of 100 ppm, and all the sulfur dioxide is reacted into sulfur trioxide, then the result is 100 ppm of sulfur trioxide. Some of the parameters include entrance flow rate, exit flow rate, temperature of the catalyst 120, surface area, and relative humidity. By way of a non-limiting example, controlling any or all of these parameters associated with generator 140 enables generation of a known concentration of sulfur trioxide gas that is accurate to about a percentage point or less. In other words, generator 140 converts about 99% of the sulfur dioxide gas into sulfur trioxide gas.

By generating sulfur trioxide gas and by knowing the concentration of the sulfur trioxide gas to such a high level of accuracy, optical cavity 180 can use this known concentration to calibrate optical cavity 180 to then be able to accurately measure concentrations of sulfur trioxide samples in flue gases.

In step 240, generator 140 maintains the generated known concentration of sulfur trioxide gas in a gaseous state. Sulfuric acid is a common reagent in the chemical industry, and important to many applications. A common method of generating sulfuric acid is to oxidize sulfur dioxide into sulfuric acid. In this process, sulfur dioxide briefly converts to sulfur trioxide before becoming sulfuric acid.

Referring to FIGS. 3 and 4, the sulfur trioxide gas generation process can include additional processing steps according to embodiments herein.

In step 210, generator 140 receives a known concentration of sulfur dioxide gas or a mixture of sulfur dioxide gas with oxygen from tank 105 through conduit 110. Valve 117-1 and/or valve 116-1 enable sulfur dioxide and agent to flow through conduit 110, while mass flow controller 152-1 controls a flow rate of sulfur dioxide into chamber 130.

In step 212, generator 140 pre-heats the sulfur dioxide gas. For example, the sulfur dioxide is potentially heated before exposing the sulfur dioxide gas to the catalyst 120. In one embodiment, conduit 110 can be wrapped with a heat source to heat the conduit 110 and received sulfur dioxide and/or agent.

In some embodiments, the source 105 maintains sulfur dioxide gas at ambient temperature such as room temperature. Preheating the sulfur dioxide gas in conduit 110 can improve reaction efficiency as mentioned above.

One of the parameters of conversion efficiency is a temperature of the reaction at the catalyst 120. If the temperature of the catalyst 120 varies over time, then conversion efficiency may vary. This temperature variation can yield a sulfur trioxide concentration that is not accurately known. Thus, control of the heater 125 to be at or above a threshold value can be useful.

In one embodiment, in step 220, generator 140 receives an oxidizing agent gas, such as oxygen, through conduit 110 as described above.

In step 230, generator 140 exposes the known concentration of sulfur dioxide gas and the oxidizing agent gas to a catalyst 120. Generator 140 heats catalyst 120 to a temperature between about 225° C. and 600° C., to react the known concentration of sulfur dioxide gas and the oxidizing agent gas into a known concentration of sulfur trioxide gas. Because the catalyst 120 is heated, the combination of received oxidizing agent and sulfur dioxide gas of known concentration are heated to between about 225° C. and 600° C. as well.

In step 232, generator 140 controls a temperature of the catalyst 120. In one embodiment, the flow rate of sulfur dioxide gas and agent are substantially constant and the temperature of the catalyst 120 is controlled to a value between 225° C. and 600° C. In such an embodiment, different amounts of dilution gas are provided though conduit 114 to produce calibration gases of varying concentrations.

In certain other example embodiments, the generator 140 controls a temperature of the catalyst 120 based on a flow rate of the known concentration of sulfur dioxide gas and the oxidizing agent gas to or through catalyst 120. For example, for higher flow rates, the generator 140 can control the temperature of the catalyst to be a higher temperature value; for lower flow rates, the generator 140 can control the temperature of the catalyst to be a lower temperature value.

Thus, a temperature of the heater 125 and/or environment 144 can vary depending on a flow rate of the gas through the oxidizing chamber 130. For example, some embodiments specify a flow rate of 2 liters per minute through oxidizing chamber 130, while other embodiments specify a flow rate of 0.2 liters per minute. Embodiments of the invention can operate with flow rates greater or less than these amounts.

For a given flow rate, there may be a corresponding optimal temperature in which to heat catalyst 120 to facilitate conversion. The optimal temperature is a temperature at which about above 90% such as 98% or 99% or more of the sulfur dioxide passing across the catalyst is converted to sulfur trioxide in the oxidizing chamber 130. The optimal temperature can vary depending on a respective flow rate. More specifically, by way of a non-limiting example, if a flow rate were 0.5 liters a minute with a water amount of less than 20 ppm (particulate-per-million), then the corresponding temperature may be about 450 C to react the sulfur dioxide at about 99%. As mentioned, the amount of water may be less than 5 ppm such as 1 ppm.

Figure 5:
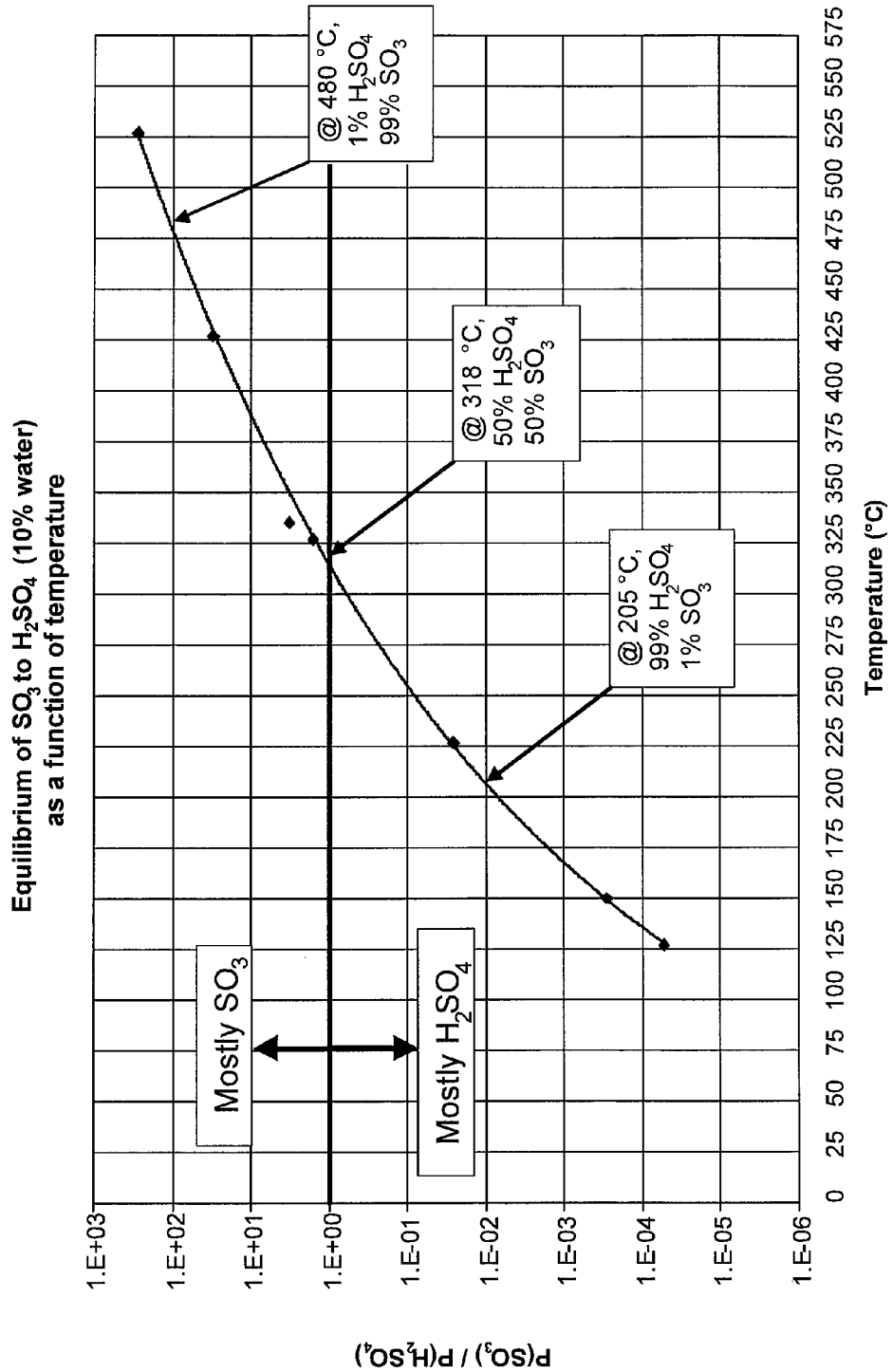
FIG. 5 is graph showing the equilibrium of sulfur trioxide and sulfuric acid at 10% water.
Figure 6:
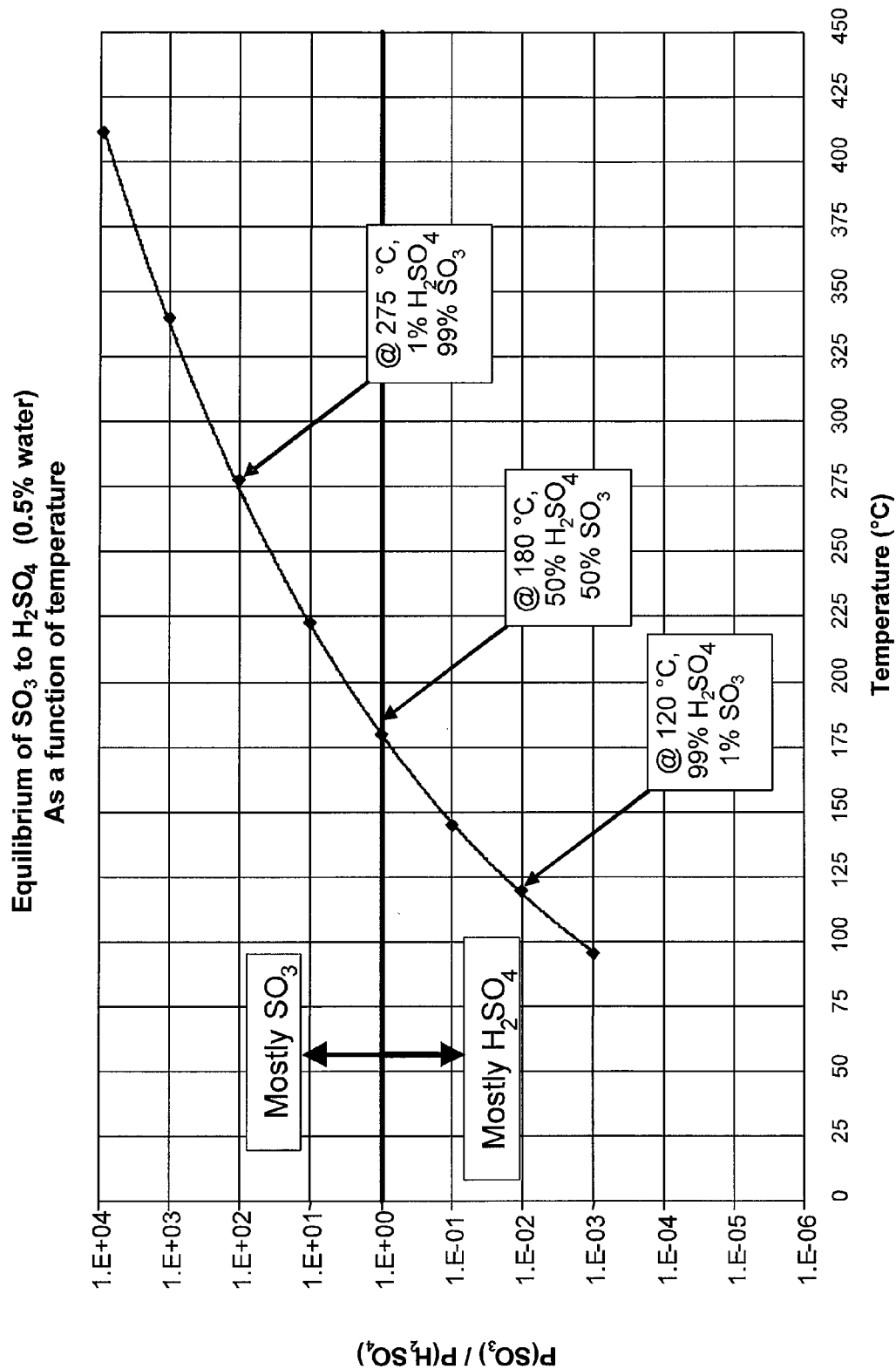
FIG. 6 is graph showing the equilibrium of sulfur trioxide and sulfuric acid at 0.5% water.

If there is any water present then sulfur trioxide may quickly condense at lower temperatures. The graphs depicted in FIGS. 5 and 6 illustrate this difficulty. FIG. 5 graphs equilibrium of sulfur trioxide and sulfuric acid as a function of temperature in an environment having 10% water in conditions of 1 atmosphere. At 205° C., only about 1% of sulfur trioxide remains while 99% became sulfuric acid. At 318° C. the balance of sulfuric acid and sulfur trioxide is about equal. At 450° C., about 99% of sulfur trioxide remains in a gaseous state. Thus, embodiments herein can include providing a water-free environment in which to perform reactions.

FIG. 6 graphs equilibrium of sulfur trioxide in sulfuric acid in an environment of 0.5% water instead of 10% water in conditions of 1 atmosphere. With relative humidity reduced, sulfur trioxide can remain in a gaseous state at a lower temperature. Sulfur trioxide exists at 99 percent with a temperature of 275° C. when the amount of water is 0.5% of the concentration of the sulfur trioxide. Thus, sulfur trioxide requires heat to remain in a gaseous state, and the amount of heat required is a function of relative humidity.

Controlling the catalyst to an optimal conversion temperature is useful because of complications from reacting sulfur dioxide at temperatures that are too low or temperatures that are too high. That is, the difficulty of maintaining sulfur trioxide as a gas at lower temperatures, and the reduction in conversion efficiency at higher temperatures means that there is an optimal temperature or temperature range for generating and maintaining sulfur trioxide gas. In most embodiments, the flow rate across catalyst 120 is constant, and thus a temperature of the catalyst is substantially constant.

In one embodiment, in step 233, generator 140 exposes the known concentration of sulfur dioxide gas and the oxidizing agent gas to catalyst 120 at different flow rates at different time periods. For example, at a first time period, mass flow controllers 152-1 and 152-2 deliver a gas mixture across catalyst 120 at a first flow rate. This first flow rate is constant. In a second time period, mass flow controllers 152-1 and 152-2 deliver a gas mixture across catalyst 120 at a second flow rate. The second flow rate is constant. In a third time period, mass flow controllers 152-1 and 152-2 deliver a gas mixture across catalyst 120 at a third flow rate, wherein the third flow rate is constant. As mentioned above, generator 140 can be configured to adjust a temperature of catalyst 120 according to the different flow rates at the different time periods to yield a conversion of sulfur dioxide gas to sulfur trioxide gas at an efficiency level above about 99%. For each flow rate there is a corresponding optimal temperature that will result in a high and/or known conversion efficiency.

In step 240, generator 140 maintains the known concentration of sulfur trioxide gas in a gaseous state. Conventional systems and methods do not exist for maintaining 99% pure sulfur trioxide that exists long enough in a gaseous state to be analyzed in order to calibrate a system that measures sulfur trioxide directly.

In step 242, generator 140 dilutes the sulfur trioxide gas with a gas such as heated air received from conduit 114. Via heated environment 145, the generator 140 maintains the diluted sulfur trioxide gas above a conversion/condensation point of sulfuric acid. As previously discussed, diluting the sulfur trioxide via gas received from source 107 changes a concentration of the sulfur trioxide in the calibration gas passing through optical cavity 180.

If desired, in an alternative embodiment, generator 140 can be configured to dilute the sulfur trioxide gas with, for example, heated air prior to passing the sample gas through the catalyst 120. Diluting the gas mixture before the conversion reaction can change the level of efficiency. Therefore, most embodiments herein involve diluting the sulfur trioxide outputted by oxidizing chamber 130 via transmission of dilution gas through conduit 114.

As mentioned above, mass flow controller 152-3 controls a dilution amount or rate. In one embodiment, the generator 140 can dilute the sulfur trioxide outputted from oxidizing chamber 130 in a range of between 1 and 25 parts of dilution gas to 1 part of sulfur trioxide calibration gas. Nominally the generator 140 dilutes at about 6 parts of dilution gas to 1 part of sulfur trioxide gas outputted from the oxidizing chamber 130. Generator 140 maintains the dilution gas substantially free of water.

In further embodiments, the optical cavity 180 is used to monitor (non-calibration type) gas samples having an unknown concentration of samples gases. It can be known in advance of an approximate setpoint concentration of the sulfur trioxide in the non-calibration gas being monitored. To facilitate more accurate generation of a sulfur trioxide concentration value for the non-calibration sample under test, embodiments herein can include diluting the sulfur trioxide calibration sample gas outputted by the oxidizing chamber 130 an appropriate amount to be equal or substantially equal to the expected amount of sulfur trioxide in the non-calibration gas sample. Calibration of the optical system at or around the setpoint value (as well as one or more other values around the setpoint value) using the one or more concentrations of calibration gas as described herein can help to ensure that the concentration value generated for the unknown sample is accurate. When multiple points are used in calibration, linear methods can be employed to provide accurate calibration of the optical system for the multiple calibration points around the setpoint.

In step 250, generator 140 passes a portion of the diluted sulfur trioxide gas, having a known concentration of sulfur trioxide gas, through optical cavity 180. Certain embodiments may not require all generated sulfur trioxide gas to pass-through optical cavity 180. In such embodiments, generator 140 directs a portion of the diluted sulfur trioxide mix to optical cavity 180, and then exhausts the remaining gas mixture outside of the system.

In step 252, generator 140 passes the diluted sulfur trioxide gas to a multi-pass optical cell that measures sulfur trioxide using a tunable diode laser. Such a multi-pass cell can be a Herriot-type optical cell, a White-type optical cell, etc. As mentioned above, the generator 140 can use oxidizing chamber 180 to measure sulfur trioxide using gas phase spectroscopy.

In step 254, generator 140 calibrates the sulfur trioxide detection device by measuring the known concentration of sulfur trioxide gas passing through the optical cavity 180, and adjusting the measurements of the optical cavity 180 to match the known concentration of sulfur trioxide gas. With such measurement and adjustment, generator 140 can measure a concentration of sulfur trioxide in samples received from, for example, a smokestack.

During operation, a condition of the catalyst 120 can degrade after use. The degraded condition may prevent the catalyst 120 from efficiently converting the received sulfur dioxide into sulfur trioxide. To restore the catalyst 120 back to a high efficiency converter, embodiments herein can include at least temporarily heating the catalyst 120 to a temperature of greater than 550 degrees Celsius. This can have the effect of burning off any impurities that have collected on a surface of the catalyst 120 during prior use to create the sulfur trioxide. Subsequent to this heating/cleaning process, the catalyst can then be used as described herein to facilitate high efficiency conversion (e.g., greater than 98%) of the sulfur dioxide into sulfur trioxide.

With some selections of catalytic materials in the tubing, catalyst 120 can degrade or produce impurities. This is also known as catalyst poisoning, meaning that the catalyst is chemically and/or physically (coating) may be altered during generation of sulfur trioxide such that the degradation reduces the usefulness or efficiency of the catalyst 120. Such degradation of the catalyst 120 can happen after days or hours of sulfur trioxide generation. This degradation, however, is reversible. In one embodiment, generator 140 reverses catalytic degradation by heating catalyst 120 above about 550° C. to reverse the catalytic degradation.

In most embodiments there is one set point, in that generator 140 operates catalyst 120 at a constant temperature and maintains a flow through the catalyst 120 to be a substantially constant flow rate, except to restore the catalyst 120 when it has no longer efficiently converts sulfur dioxide into sulfur trioxide. As mentioned, generator 140 can adjust temperature and flow rates. The set point can change based on various applications. For example, if a plant changes from a coal-fired system to a combustible fuel that generates more or less sulfur trioxide, or to another industrial process that generates higher levels of sulfur trioxide, then in one embodiment generator 140 adjusts flow rates and/or temperatures accordingly. In another embodiment, generator 140 uses source 105, which has a higher concentration of sulfur dioxide. In another embodiment, as mentioned above, generator 140 can be configured to dilute sulfur trioxide calibration gas to a concentration that approximates amounts of sulfur trioxide gas from sample flue gases for more accurate readings.

As previously mentioned, the generator 140 can include a hydrator 108 to aid in conversion of sulfur trioxide to sulfuric acid. Such conversion to sulfuric acid can be useful for embodiments that include both a sulfur trioxide detection device and a sulfuric acid detection device. Thus, embodiments herein can include producing a sulfur trioxide calibration gas as well as producing sulfuric acid for calibration purposes. In the latter instance, the temperature of environments 144 and 145 can be reduced in order to encourage conversion of the sulfur dioxide and/or sulfur trioxide into sulfuric acid. By adding dihydrogen monoxide ($H_2O$), also known as water, to the generated sulfur trioxide gas, sulfur trioxide gas converts to sulfuric acid. Generator 140 can add water, or increases relative humidity, by opening valve 116-4 to add water to generated sulfur trioxide. Thus, generator 140 can adjust the balance between sulfuric acid and sulfur trioxide by controlling an amount of humidity, and by controlling the temperature.

While it may be relatively easy to create sulfuric acid, sulfuric acid may be difficult to measure. If desired, generator 140 can be configured to convert sulfuric acid to sulfur trioxide by heating the sulfuric acid to a temperature sufficiently hot (and remove water) to convert the sulfuric acid to sulfur trioxide gas.

A location of the generator 140 provides several advantages. In one embodiment, generator 140 generates and maintains sulfur trioxide gas less than about six feet from the optical cavity 180. Additionally, generator 140 and optical cavity 180 are both located within a flue gas measurement probe configured to attach to a flue gas system, chimney, or exhaust stack. Having generator 140 located at a point of injection inside the probe is beneficial. By heating the entire probe, generator 140 maintains sulfur trioxide in a gaseous state after passing through the chamber 130. For example, the probe can maintain an internal temperature above a dew point of sulfuric acid. Usually there is some measure of water in the system, and so keeping the probe at a high temperature helps maintain sulfur trioxide in a gaseous state and prevent conversion to sulfuric acid. In addition to overall system heating, air dryer 108 helps maintain low levels of humidity.

Referring again to the example embodiment of FIG. 1, chamber 130 is illustrated to emphasize a construction catalyst 120, and thus appears to have a diameter larger than conduits 110, 112, and 117, although such construction is optional in physical embodiments. In one embodiment, note that the oxidizing chamber 130 has a cross-sectional area that is approximately equal to a cross sectional area of conduits used as input and out put of chamber. In alternative embodiments, chamber 130 can have a cross sectional area sized larger or small than conduits of generator 140.

In an example embodiment, the catalyst 120 has a surface area sufficiently large for the known concentration of sulfur dioxide gas to react and produce a known concentration of sulfur trioxide gas at an efficiency above about 99%. By way of a non-limiting example, for a flow rate of 0.2 Liters per minute, the amount of catalyst 120 needed is 5 grams.

The system can include a catalyst 120 configured in one of multiple different ways. In one configuration, catalyst 120 includes several relatively small and loose metallic particles. To help direct sulfur dioxide gas and oxidizing agent gas through or across the catalytic material, a pair of porous frits 127 position such loose catalytic material to fill a cross-section within chamber 130. The pair of porous fits 127 essentially act as plugs or bookends to position a loose catalytic material such as to maximize contact with the mixed gases.

For example, the frits 127 can be sintered metal. Because frits 127 are porous, mixed gases can pass through a first frit 127-1, across the catalyst 120, and through a second frit 127-2 as sulfur trioxide gas. Such catalytic material can be made of platinum, palladium, vanadium, nickel, iron oxide, etc.

In another embodiment, generator 140 is a relatively small form factor. Most sulfuric acid production facilities include large chemical reaction equipment. In contrast, the sulfur trioxide gas generation system can fit within a probe that occupies less than about 6 cubic feet of volume, while the chamber 130 can be sized to occupy less than about one cubic foot of space.

Although the methods and systems have been described relative to a specific embodiment, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Accordingly, it is submitted that that the invention should not be limited to the described embodiments but rather should be limited only by the spirit and scope of the appended claims.

What is claimed is:

1. A method comprising:
   receiving a known concentration of sulfur dioxide gas;
   receiving an oxidizing agent gas;
   controlling the known concentration of sulfur dioxide gas and the oxidizing agent gas to be substantially free of water;
   conveying the known concentration of sulfur dioxide gas and the oxidizing agent gas, which are substantially free of water, to a reaction chamber;
   exposing the known concentration of sulfur dioxide gas and the oxidizing agent gas to a catalyst in the reaction chamber, the catalyst being heated, to react the known concentration of sulfur dioxide gas and the oxidizing agent gas into a known concentration of sulfur trioxide gas; and
   maintaining the known concentration of sulfur trioxide gas in a gaseous state.

2. The method of claim 1, wherein maintaining the known concentration of sulfur trioxide gas in the gaseous state includes:
   diluting the sulfur trioxide gas with a dilution gas, the dilution gas being substantially free of water; and
   maintaining the diluted sulfur trioxide gas above a conversion point temperature of sulfuric acid.

3. The method of claim 2, further comprising:
   passing a portion of the diluted sulfur trioxide gas, having a known concentration of sulfur trioxide gas, through a sulfur trioxide detection device.

4. The method of claim 3, wherein passing the portion of the diluted sulfur trioxide gas, having a known concentration of sulfur trioxide gas, through the sulfur trioxide detection device includes:
   passing the diluted sulfur trioxide gas through a multi-pass optical cell that measures a concentration of sulfur trioxide.

5. The method of claim 3, further comprising:
   calibrating the sulfur trioxide detection device by measuring the known concentration of sulfur trioxide gas passing through the sulfur trioxide detection device; and
   adjusting measurements of the sulfur trioxide detection device based on calibration using the known concentration of sulfur trioxide gas.

6. The method as in claim 5 further comprising:
   exposing the known concentration of sulfur trioxide gas to water to convert the sulfur trioxide gas into sulfuric acid; and
   utilizing the sulfuric acid for calibration.

7. The method of claim 1, wherein receiving the known concentration of sulfur dioxide gas includes pre-heating the sulfur dioxide gas before exposing the sulfur dioxide gas to the catalyst.

8. The method of claim 1, further comprising:
   heating the catalyst to above about 550 degrees Celsius to restore a degraded condition of the catalyst, the degraded condition causing reduced efficiency of converting the sulfur dioxide into the sulfur trioxide.

9. The method of claim 1, wherein exposing the known concentration of sulfur dioxide gas and the oxidizing agent gas to a catalyst includes heating the catalyst to a temperature between 225 degrees Celsius and 600 degrees Celsius.

10. The method of claim 1, wherein exposing the known concentration of sulfur dioxide gas and the oxidizing agent gas to a catalyst includes:
    exposing the known concentration of sulfur dioxide gas and the oxidizing agent gas to a catalyst at different flow rates at different time periods; and
    adjusting the temperature of the catalyst according to the different flow rates at the different time periods to yield a conversion of the sulfur dioxide gas to the sulfur trioxide gas at an efficiency level above about 99%.

11. The method of claim 1, further comprising:
    converting the sulfur trioxide gas to sulfuric acid by adding dihydrogen monoxide; and
    heating the sulfuric acid to a temperature sufficient to convert the sulfuric acid to sulfur trioxide gas.

12. The method of claim 1, wherein a generator that performs the method of converting the sulfur dioxide gas to sulfur trioxide gas is disposed less than about 6 feet from a sulfur trioxide detection device.

13. The method as in claim 1 further comprising:
    preventing exposure of the sulfur trioxide gas produced in the reaction chamber to water.

14. The method of claim 13, further comprising:
    adjusting dilution of the sulfur trioxide with the dilution gas to produce different concentrations of sulfur trioxide gas; and
    performing a multi-point calibration of a sulfur trioxide detection device by measuring the different concentrations of sulfur trioxide gas passing through the sulfur trioxide detection device.

15. The method of claim 14, wherein exposing the known concentration of sulfur dioxide gas and the oxidizing agent gas to a catalyst includes heating the catalyst to a temperature between 225 degrees Celsius and 600 degrees Celsius.

16. The method of claim 15, wherein exposing the known concentration of sulfur dioxide gas and the oxidizing agent gas to the catalyst includes:
    exposing the known concentration of sulfur dioxide gas and the oxidizing agent gas to the catalyst at different flow rates at different time periods; and
    adjusting the temperature of the catalyst according to the different flow rates at the different time periods to yield a conversion of sulfur dioxide gas to sulfur trioxide gas at an efficiency level above about 99%.

17. The method of claim 16, further comprising:
heating the catalyst to above about 550 degrees Celsius to restore a degraded condition of the catalyst, the degraded condition causing reduced efficiency of converting the sulfur dioxide into the sulfur trioxide.

18. The method of claim 13 further comprising:
to maintain a desired conversion efficiency of converting the sulfur dioxide gas into the sulfur trioxide gas, adjusting a temperature of heating the catalyst depending on a flow rate of inputting the known concentration of sulfur dioxide through the catalyst.

19. The method of claim 13 further comprising:
controlling flow rates of the sulfur dioxide gas and oxidizing agent gas and controlling the temperature of the catalyst to control a conversion efficiency of converting the known concentration of sulfur dioxide gas into the known concentration of the sulfur trioxide gas, the conversion efficiency controlled to an accuracy of less than a percentage point, the reaction chamber converting above about 99% of the sulfur dioxide gas into sulfur trioxide gas.

20. The method of claim 19 further comprising:
heating the catalyst to above about 550 degrees Celsius to restore a degraded condition of the catalyst, the degraded condition causing reduced efficiency of converting the sulfur dioxide into the sulfur trioxide;
wherein exposing the known concentration of sulfur dioxide gas and the oxidizing agent gas to the catalyst includes heating the catalyst to a temperature between 225 degrees Celsius and 600 degrees Celsius;
wherein exposing the known concentration of sulfur dioxide gas and the oxidizing agent gas to the catalyst includes:
exposing the known concentration of sulfur dioxide gas and the oxidizing agent gas to the catalyst at different flow rates at different time periods; and
adjusting the temperature of the catalyst according to the different flow rates at the different time periods to yield a conversion of sulfur dioxide gas to sulfur trioxide gas at an efficiency level above about 99%.

21. The method of claim 1, further comprising:
wherein maintaining the known concentration of sulfur trioxide gas in the gaseous state includes maintaining the sulfur trioxide gas above a conversion point temperature of sulfuric acid;
passing a portion of the sulfur trioxide gas through a sulfur trioxide detection device, the sulfur trioxide detection device being a device that measures a concentration of sulfur trioxide;
wherein receiving the known concentration of sulfur dioxide gas includes pre-heating the sulfur dioxide gas before exposing the sulfur dioxide gas to the catalyst;
wherein exposing the known concentration of sulfur dioxide gas and the oxidizing agent gas to the catalyst includes heating the catalyst to a temperature between 225 degrees Celsius and 600 degrees Celsius; and
heating the catalyst to above about 550 degrees Celsius to restore a degraded condition of the catalyst, the degraded condition causing reduced efficiency of converting the sulfur dioxide into the sulfur trioxide.

22. The method of claim 1, wherein maintaining the known concentration of sulfur trioxide gas in the gaseous state includes:
outputting sulfur trioxide gas from the reaction chamber;
diluting the outputted sulfur trioxide gas with a dilution gas, the dilution gas being substantially free of water;
hydrating the diluted sulfur trioxide gas; and
heating a conduit through which the hydrated diluted sulfur trioxide gas is conveyed to an analyzer, the conduit heated to a sufficiently high temperature to prevent conversion of the hydrated diluted sulfur trioxide gas into sulfuric acid.

23. The method as in claim 22 further comprising:
preventing exposure of the sulfur trioxide gas produced in the reaction chamber to water.

* * * * *